United States Patent
Vasant Rode et al.

(10) Patent No.: US 10,428,038 B2
(45) Date of Patent: Oct. 1, 2019

(54) SINGLE STEP PROCESS FOR THE SYNTHESIS OF FURFURYL ETHYL ETHER

(71) Applicant: COUNCIL OF SCIENTIFIC AND INDUSTRIAL RESEARCH, New Delhi (IN)

(72) Inventors: Chandrashekhar Vasant Rode, Pune (IN); Chetana Rupak Patil, Pune (IN)

(73) Assignee: COUNCIL OF SCIENTIFIC AND INDUSTRIAL RESEARCH, New Dehli (IN)

( * ) Notice: Subject to any disclaimer, the term of this patent is extended or adjusted under 35 U.S.C. 154(b) by 0 days.

(21) Appl. No.: 16/251,671

(22) Filed: Jan. 18, 2019

(65) Prior Publication Data

US 2019/0218195 A1    Jul. 18, 2019

(30) Foreign Application Priority Data

Feb. 26, 2018 (IN) .............................. 201811007111

(51) Int. Cl.
C07D 307/42 (2006.01)
B01J 29/04 (2006.01)

(52) U.S. Cl.
CPC .......... *C07D 307/42* (2013.01); *B01J 29/041* (2013.01)

(58) Field of Classification Search
CPC .................................................. C07D 3017/42
USPC .......................................................... 549/497
See application file for complete search history.

(56) References Cited

U.S. PATENT DOCUMENTS

2011/0035991 A1    2/2011  Haan

*Primary Examiner* — Patricia L Morris
(74) *Attorney, Agent, or Firm* — Cantor Colburn LLP

(57) ABSTRACT

The present invention provides a single step process for the synthesis of furfuryl ethyl ether comprises refluxing the reaction mixture of furfuryl alcohol, ethanol and catalyst at temperature in the range of 80 to 120° C. for the period in the range of 3 to 7 hrs to afford furfuryl ethyl ether. The catalyst used in present invention is Zr incorporated SBA-15. Further, the conversion of furfuryl alcohol is in the range of 60 to 90%. The selectivity of reaction towards furfuryl ethyl ether is in the range of 85 to 95%.

4 Claims, 12 Drawing Sheets

SINGLE STEP PROCESS FOR THE SYNTHESIS OF FURFURYL ETHYL ETHER

CROSS REFERENCE TO RELATED APPLICATION

This application is related to and claims the benefit of Indian Patent Application Number 201811007111 filed on Jan. 18, 2018, the entire content of which is incorporated herein by reference.

FIELD OF THE INVENTION

The present invention relates to a process for the synthesis of furfuryl alkyl ether. More particularly, the present invention relates to a single step process for the synthesis of furfuryl ethyl ether from furyl alcohol in presence of mesoporous Zr-incorporated SBA-15 catalyst.

BACKGROUND AND PRIOR ART

Furfuryl ethyl ether (FEE) is a bio-based transportation fuel component and an important blend in gasoline. FEE has superior anti-knock quality to the reference Euro95 gasoline. Furfuryl ethyl ether is an important flavor compound indicative of beer storage and aging conditions. Furfuryl alcohol found to be best platform molecule for the synthesis of FEE. Mild acidic conditions are responsible for conversion of furfuryl alcohol to FEE. Powdered ZSM-5 catalyst ($SiO_2/Al_2O_3=30$) operating at 125° C. in a 7.5:1 molar mixture of EtOH: FAlc, furfuryl ethyl ether was formed with a maximum yield of 50 mol % yield at ~80% conversion. Other zeolites, e.g. with H-ZSM-12 and -23, H-β ($SiO_2$-bound), H-Y, H-Mordenite and H-Ferrierite, showed significantly lower yields towards FEE. Mesoporous silica material like, SBA-15 having large pore size, high surface area, hexagonally ordered structure, thick pore wall, and remarkable hydrothermal stability and more importantly, easy preparation protocol, becomes the choice of preference.

US2011035991 discloses a gasoline composition containing in the range of from 0.1 to 30 wt % alkylfurfuryl ether with an alkyl group having 1 to 4 carbon atoms is provided. The gasoline composition is prepared by blending the alkylfurfuryl ether in a gasoline base fuel. The alkylfurfuryl ether is prepared by reacting an alkyl alcohol having in the range of 1 to 4 carbon atoms is reacted with furfuryl alcohol by contacting a liquid phase comprising the alkyl alcohol and furfuryl alcohol with an acidic zeolite catalyst at a temperature in the range of from 50 to 200° C. This document further discloses use of ZSM-5 for synthesis of FEE got 80 to 95% conversion of Furfuryl alcohol but the yield of FEE is less i. e 27%. Yield of Furfuryl alcohol condensation product is 27% which is due to presence of Bronsted acidity in ZSM-5 catalyst.

Article titled "The effect of oxide acidity on HMF etherification" by J Luo et al. published in *Catal. Sci. Technol.*, 2014, 4, pp 3074-3081 reports liquid-phase (69 bar) reaction of 5-hydroxymethylfurfural (HMF) with 2-propanol for production of furanyl ethers studied at 413 and 453 K over a series of oxide catalysts, including γ-$Al_2O_3$, $ZrO_2$, $TiO_2$, $Al_2O_3$/SBA-15, $ZrO_2$/SBA-15, $TiO_2$/SBA-15, H-BEA, and Sn-BEA. The Lewis-acid sites on Sn-BEA were the most active, showing a high selectivity to 2,5-bis[(1-methylethoxy)methyl]furan (BEF) even at low total conversions. Interestingly, $ZrO_2$ and $TiO_2$ on SBA-15 were also quite selective towards formation of BEF, presumably by carrying the MPV interhydride transfer from 2-propanol to the carbonyl of HMF on the Lewis acid sites followed by etherification on the Brønsted acid sites of the catalyst.

Article titled "Zr-SBA-15 Lewis Acid Catalyst: Activity in Meerwein Ponndorf Verley Reduction" by J Iglesias et al. published in *Catalysts;* 2015, 5(4), pp 1911-1927 reports Zr-SBA-15 Lewis acid catalyst for outstanding catalytic activity in the reduction of several carbonyl compounds by means of Meerwein Ponndorf Verley (MPV) reaction, using several secondary alcohols, and showing a very high selectivity towards the desired products. Special focus was addressed in the catalytic activity of Zr-SBA-15 material in the production of furfuryl alcohol from furfural, which is an important reaction for the lignocellulosic biomass valorization. In this transformation, both the reaction temperature and the i-PrOH:Furfural molar ratio exerts a positive influence on the rate of the MPV transformation, with the influence of the former being much higher.

The prior art suffers from the drawbacks like use of harsh chemicals, lower yield of FEE and lesser conversion of furfuryl alcohol. Therefore, there is need for a simple process for the synthesis of FEE with high yield and which will overcome prior art drawbacks. Accordingly, the present invention provides a single step process for the synthesis of furfuryl ethyl ether from furfuryl alcohol.

OBJECTIVE OF INVENTION

The main objective of the present invention is to provide an environment friendly single step process for the synthesis of furfuryl ethyl ether from furfuryl alcohol.

SUMMARY OF THE INVENTION

Accordingly, the present invention provides a single step process for the synthesis of furfuryl ethyl ether comprises refluxing the reaction mixture of furfuryl alcohol, ethanol and catalyst at temperature in the range of 80 to 120° C. for the period in the range of 3 to 7 hrs to afford furfuryl ethyl ether.

The catalyst is Zr incorporated SBA-15.

The conversion of furfuryl alcohol is in the range of 60 to 90%.

The selectivity of reaction towards furfuryl ethyl ether is in the range of 85 to 95%.

DETAILED DESCRIPTION OF THE INVENTION

The invention will now be described in detail in connection with certain preferred and optional embodiments, so that various aspects thereof may be more fully understood and appreciated.

In view of the above, the present invention provides a single step process for the synthesis of furfuryl alkyl ether from furfuryl alcohol in presence of Zr incorporated SBA-15 catalyst. The synthesis of Zr incorporated SBA-15 is carried out by direct synthesis method in self-generated acidic conditions. Incorporation of Zr improves the acidity of prepared catalyst. The prepared catalysts are tested for the etherification of furfuryl alcohol to give ethers which are proven gasoline fuel blends. Detail studies on the catalyst characterization by XRD, $^{29}$Si NMR, TEM-FFT, NH$_3$-TPD, py-IR along with effect of reaction parameters on furfuryl alcohol conversion and selectivity for ethers have been carried out.

In an embodiment, the present invention provides a single step process for the synthesis of furfuryl ethyl ether comprises refluxing the reaction mixture of furfuryl alcohol, ethanol and catalyst at temperature in the range of 80 to 120° C. for the period in the range of 3 to 7 hrs to afford corresponding furfuryl ethyl ether.

The catalyst is Zr incorporated SBA-15 and the conversion of furfuryl alcohol is in the range of 60 to 90%. The selectivity of said reaction towards furfuryl ethyl ether is in the range of 85 to 95%.

In one embodiment, the present invention provides a synthesis of Zr incorporated SBA-15 using direct synthesis method in self-generated acidic conditions. The incorporation of Zr improves the acidity of prepared catalyst. It is observed that the incorporation of Zr generates Lewis acidic sites responsible for etherification of furfuryl alcohol to FEE. It also possesses highly ordered uniform hexagonal mesochannels with high surface area 1084 m$^2$/g which minimize diffusion constraint for reactant and product. Zr-SBA-15(0.09) showed the highest conversion for furfuryl alcohol 85% with 95% selectivity towards FEE.

The process for the synthesis of furfuryl ethyl ether from furfuryl alcohol is as shown in scheme 1 below:

Scheme 1: Etherification of Furfuryl alcohol to Furfuryl ethyl ether

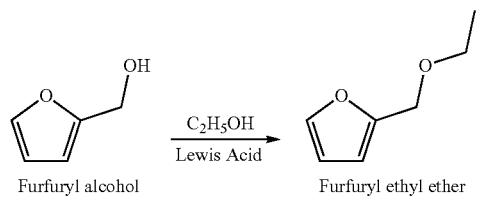

Furfuryl alcohol     Furfuryl ethyl ether

Figure 1:
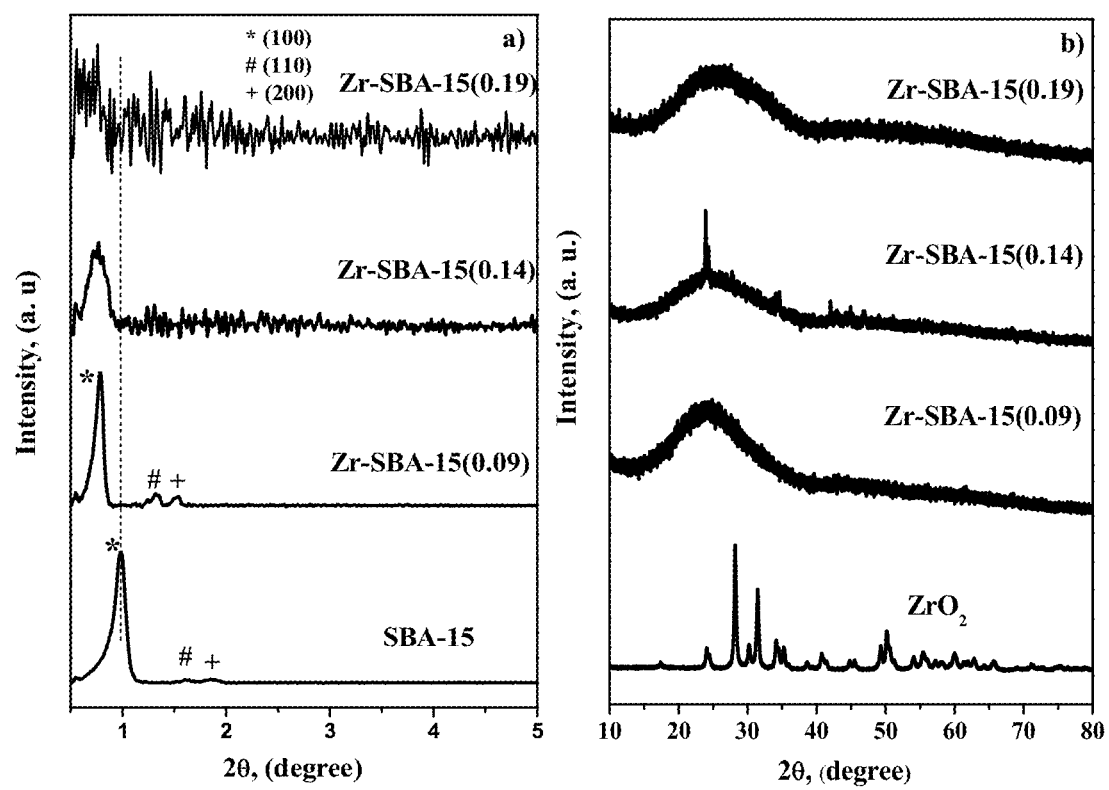
FIG. 1: Powder XRD pattern a) Low angle XRD b) Wide angle XRD for calcined Zr-SBA-15 catalysts.

The FIG. 1a) shows low angle powder XRD pattern for of calcined Zr-SBA-15 materials with different Zr loadings. Pure SBA-15 catalyst has strong (100), (110) and (200) diffraction peaks, a strong peak at around 2θ=0.8° and two small peaks at 2θ=1.6°, 1.8° respectively of 2D-hexagonal p6 mm structure, indicating that the materials possess well-ordered pore arrangement. Low angle XRD pattern of Zr-SBA-15(0.09) shows shifting of these three (100), (200) and (210) planes to lower 2θ values. This shift is because of increase in the d-spacing which confirmed the incorporation of Zr into the SBA-15 framework. This indicated that Zr is incorporated in the SBA-15 framework successfully, using one step sol-gel method which did not destroy the mesoporous structure of SBA-15. While further increase in Zr loading in case of Zr-SBA-15(0.14) and Zr-SBA-15(0.19) did not show the characteristic peaks of SBA-15 which indicates that more concentration of Zr affect the pore ordering. Wide angle powder XRD pattern for Zr-SBA-15 (0.09) showed a broad diffraction peak at 2θ around 15-35°, which is corresponding to amorphous silica walls of mesoporous materials. As no any characteristic peaks of ZrO$_2$ are observed in, it proved that Zr is incorporated into the framework of the SBA-15.

Figure 2:
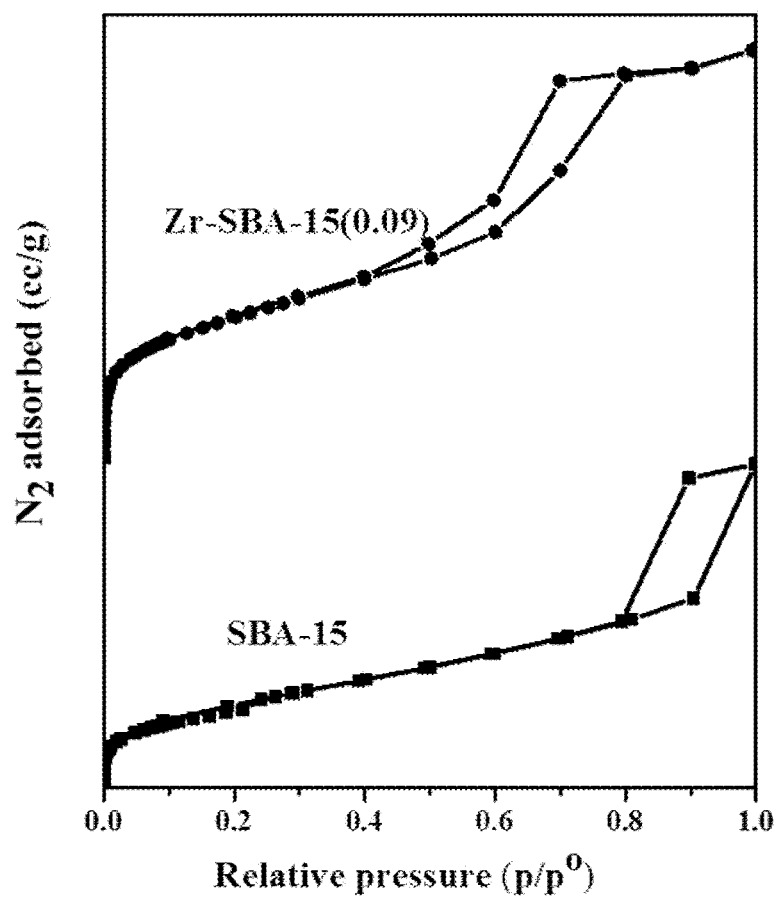
FIG. 2: Low temperature nitrogen adsorption-desorption isotherms for SBA-15 and Zr-SBA-15 (0.09)

The FIG. 2 shows the nitrogen adsorption-desorption isotherms for SBA-15 and Zr-SBA-15(0.09). Both the samples show typical type IV isotherm with H1 type hysteresis loop which is characteristic of the mesoporous nature of solids. Physicochemical properties of prepared catalysts are given in Table 1. The SBA-15 have surface area 1210 m$^2$/g while incorporation of Zr decreases the surface area to 1084 m$^2$/g along with decrease in pore volume and pore diameter from 0.75 to 0.66 (cc/g) and 18.01 to 17.96 (Å) respectively. These results suggest that Zr species are incorporated into the silica framework of SBA-15 without disturbing mesoporous structure.

TABLE 1

Physicochemical properties of the catalysts

| Sr. no. | Catalyst | Surface area$^a$ (m$^2$/g) | Pore volume$^b$ (cc/g) | Pore diameter$^b$ (Å) | Total NH$_3$ desorbed$^c$ (mmol/g) |
|---|---|---|---|---|---|
| 1 | SBA-15 | 1210 | 0.75 | 18.01 | — |
| 2 | Zr-SBA15(0.09) | 1084 | 0.66 | 17.96 | 0.11 |

$^a$multipoint BET surface area;
$^b$BJH method,
$^c$NH$_3$-TPD: NH$_3$ desorbed in the range of 200-350° C.

Figure 3:
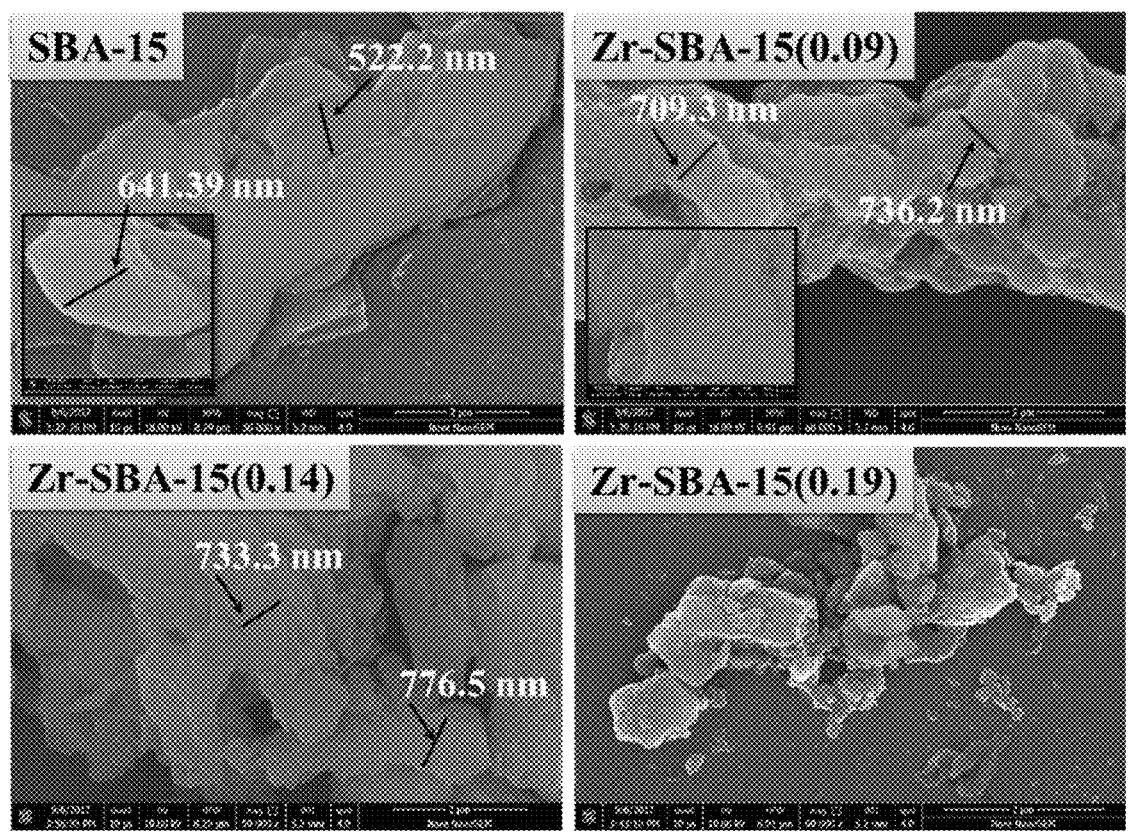
FIG. 3: Scanning electron micrographs for a) SBA-15 b) Zr-SBA-15(0.09) c) Zr-SBA-15(0.14) and d) Zr-SBA-15 (0.19)

The FE-SEM images of SBA-15 and Zr-incorporated SBA-15 catalysts are showed in FIG. 3. The parent SBA-15 catalyst showed rod like morphology FIG. 3 a). While Zr-SBA-15(0.09) FIG. 3 b) showed rope like morphology due to presence of Zr in the silica matrix. Further increase in zirconia concentration during the synthesis causes shortening of the rod like structure for Zr-SBA-115(0.14) FIG. 3 c), while it completely disrupts for Zr-SBA-15(0.19) FIG. 3 d). Elemental analysis for the SBA-15 and prepared catalyst are given in Table 2. Increase in % incorporation of Zr showed increase in the Zr/Si mole ratio.

TABLE 2

Element detection using EDAX

| Sr. No. | Catalyst | Zr/Si Molar ratio in gel | Zr/Si Molar ratio in formed catalyst |
|---|---|---|---|
| 1 | SBA-15 | 0 | 0 |
| 2 | Zr-SBA-15(0.09) | 0.09 | 0.12 |
| 3 | Zr-SBA-15(0.14) | 0.14 | 0.15 |
| 4 | Zr-SBA-15(0.19) | 0.19 | 0.19 |

Figure 4:
FIG. 4: Transmission electron micrographs for a) SBA-15 b) Zr-SBA-15(0.09) c) Zr-SBA-15(0.14) and d) Zr-SBA-15 (0.19)

The FIG. 4 shows TEM images of SBA-15, Zr-SBA-15 (0.09), Zr-SBA-15(0.14), Zr-SBA-15(0.19) catalyst with fast fourier transform images (FFT) inset Zr-SBA-15(0.09). The Zr-SBA-15(0.09) catalyst is found to retain the hexagonally ordered porous structure even after addition of Zr during synthesis. $ZrO_2$ crystals are not visible in the TEM images of confirming that Zr are not deposited on the external surface but instead are present inside the mesochannels of SBA-15. The FFT images of the high resolution TEM showed single set of six spots suggesting that the pores remained in the ordered structure throughout the volume of particles. Other FFT image viewed in [110] direction with two-fold symmetry confirmed the ordered mesoporous structure with a single dominant direction through the particle. Selected area electron diffraction (SAED) pattern confirmed that the composite matrix is composed of several mesopores which is commonly found in the amorphous materials.

Figure 5:
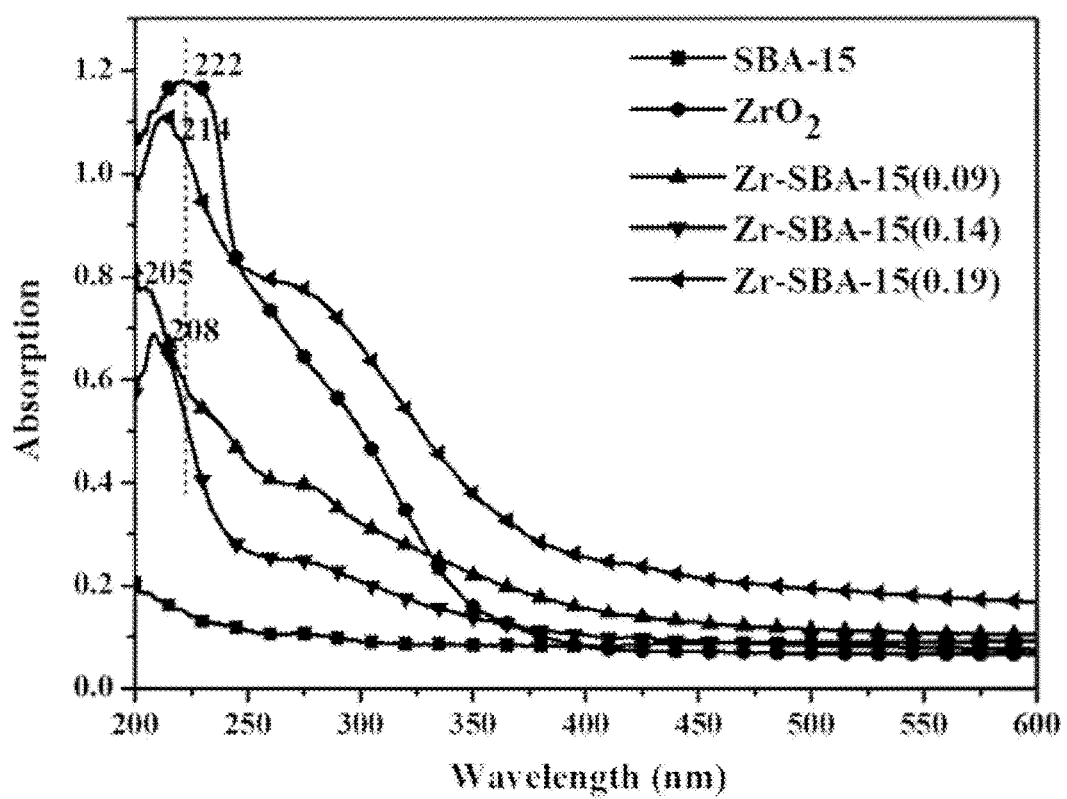
FIG. 5: DR-UV-vis spectra.

FIG. 5 shows DR-UV-vis spectra of SBA-15, $ZrO_2$ and Zr incorporated SBA-15 catalysts. In the case of Zr-SBA-15 (0.09) catalyst showed sharp absorption band at around 200-210 nm was attributed to the LMCT from $O^{2-}$ to an isolated $Zr^{4+}$ ion in a tetrahedral configuration.

Figure 6:
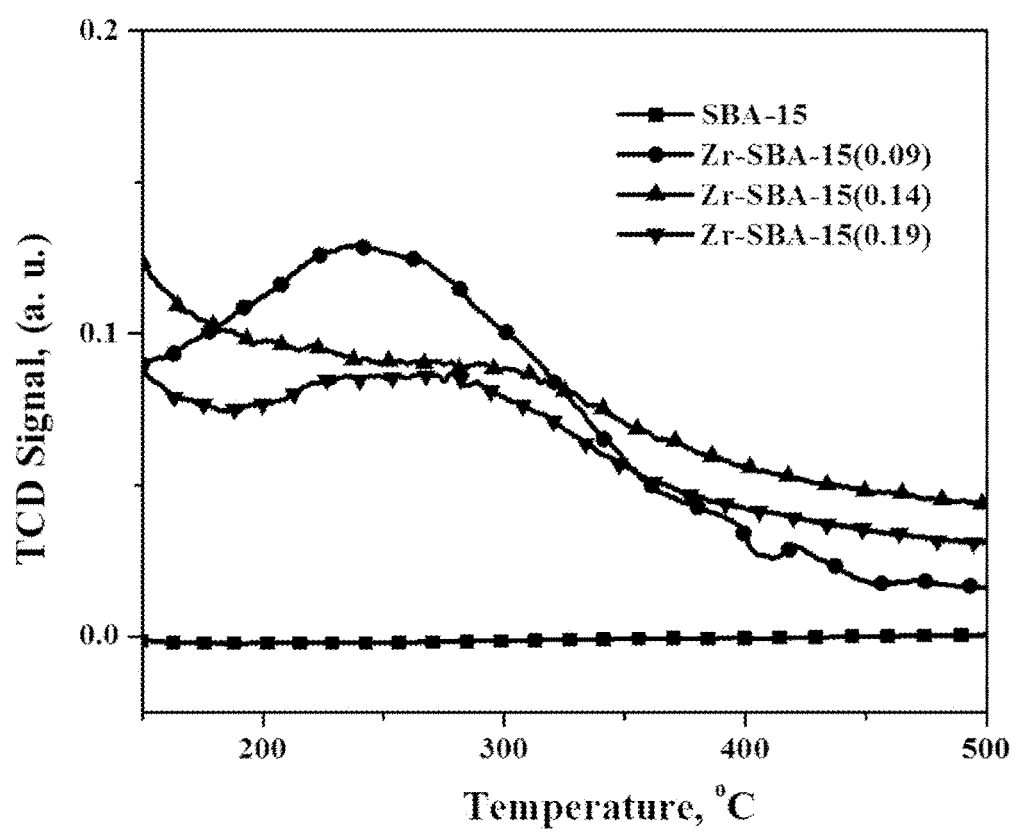
FIG. 6: $NH_3$-TPD profiles for SBA-15, Zr-SBA-15(0.09), Zr-SBA-15(0.14) and Zr-SBA-15(0.19)
Figure 7:
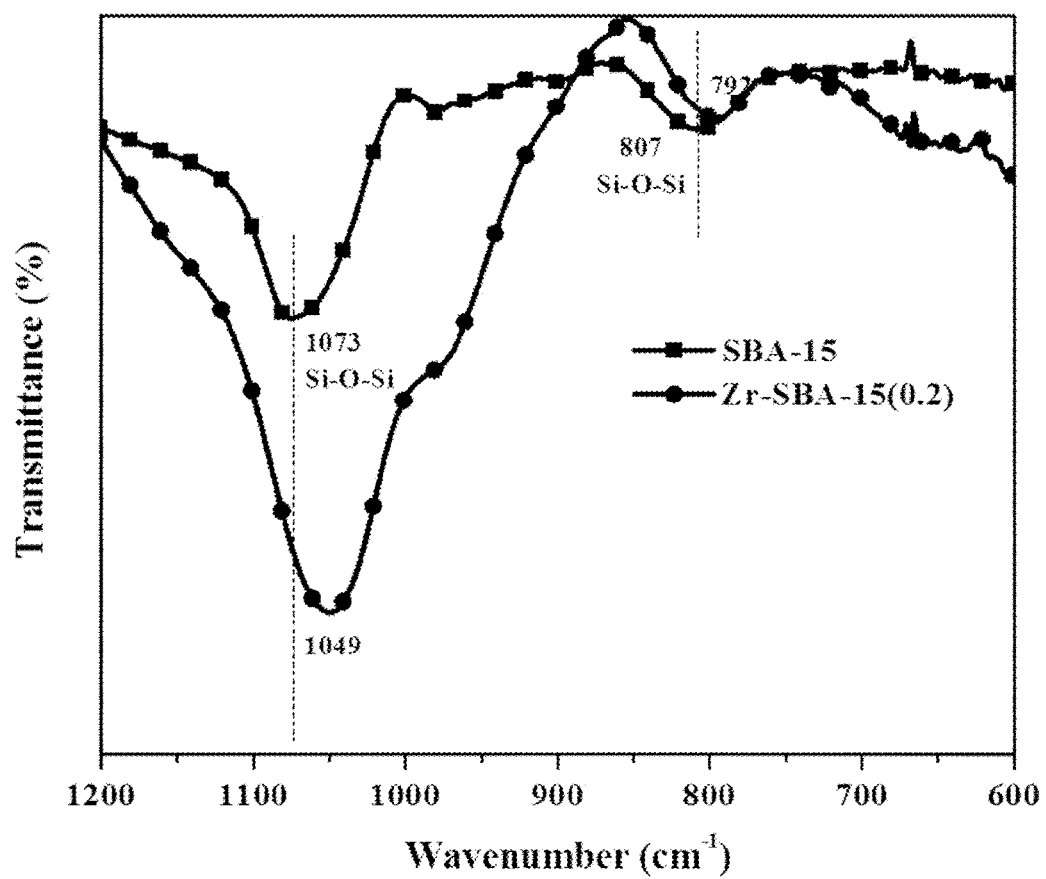
FIG. 7: FT-IR Spectra for SBA-15 and Zr-SBA-15(0.09)

The profiles of $NH_3$ temperature-programmed desorption are shown in FIG. 6. $NH_3$-TPD of SBA-15 and composite samples showed two characteristic peaks. The first peak in the region of 100-200° C. is due to the weak acidity corresponding to desorption of weakly held, physisorbed ammonia. A broad peak in the region of 200-350° C. in the Zr incorporated sample indicated the presence of weak acid sites. Zr-SBA-15(0.09) catalyst possess weak acidity 0.11 mmol/g. The FT-IR spectra for Parent SBA-15 and Zr-SBA-15(0.09) are shown in FIG. 7. SBA-15 showed two bands at 1073 $cm^{-1}$ due to asymmetric stretching mode of Si—O—Si and at 807 $cm^{-1}$ ascribed to symmetric stretching mode of Si—O—Si. Zr incorporated catalyst showed slight red shift to 1049 $cm^{-1}$ for the band at 1073 $cm^{-1}$ that evidenced the strong interaction between Zr and SBA-15.

Figure 8:
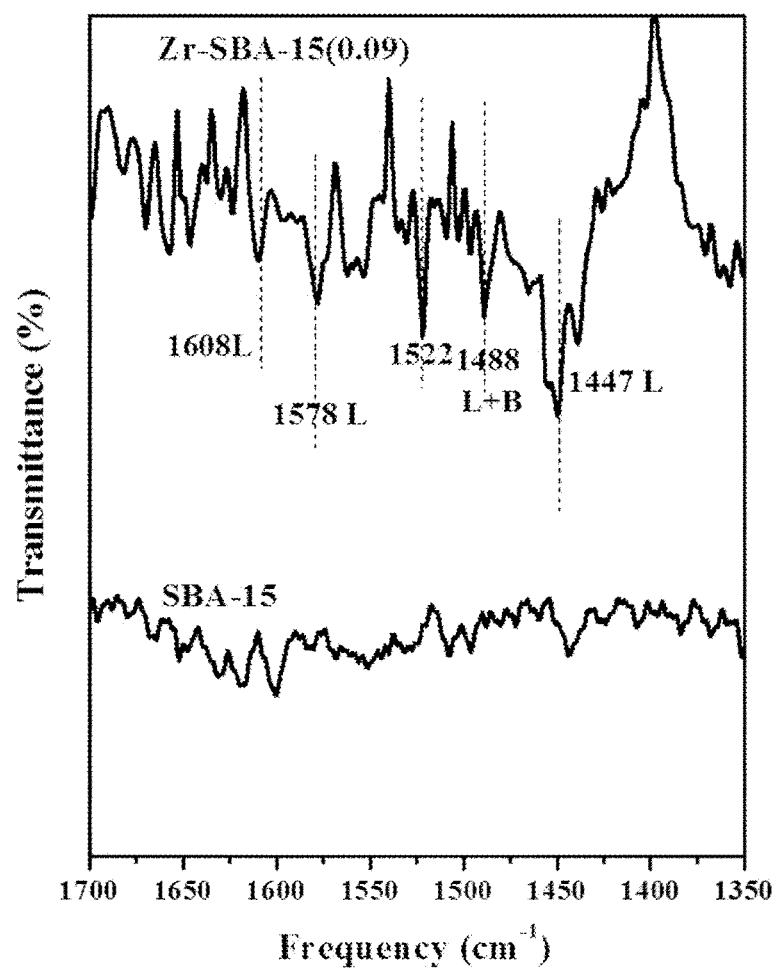
FIG. 8: py-IR Spectra for SBA-15 and Zr-SBA-15(0.09)

The FIG. 8 represents Py-IR Spectra for SBA-15 and Zr-SBA-15(0.09) catalyst to distinguish between Lewis and Brønsted acid sites. Pure SBA-15 did not show any peak for Brønsted and Lewis acid site confirming SBA-15 lacks acidic nature while Zr-SBA-15(0.09) showed peaks at 1608 $cm^{-1}$, 1578 $cm^{-1}$, 1522 $cm^{-1}$, 1488 $cm^{-1}$, 1447 $cm^{-1}$ confirming the Lewis acid sites present in the catalyst. Incorporation of Zr in the silica framework is responsible generation of Lewis acidity in the catalyst.

Figure 9:
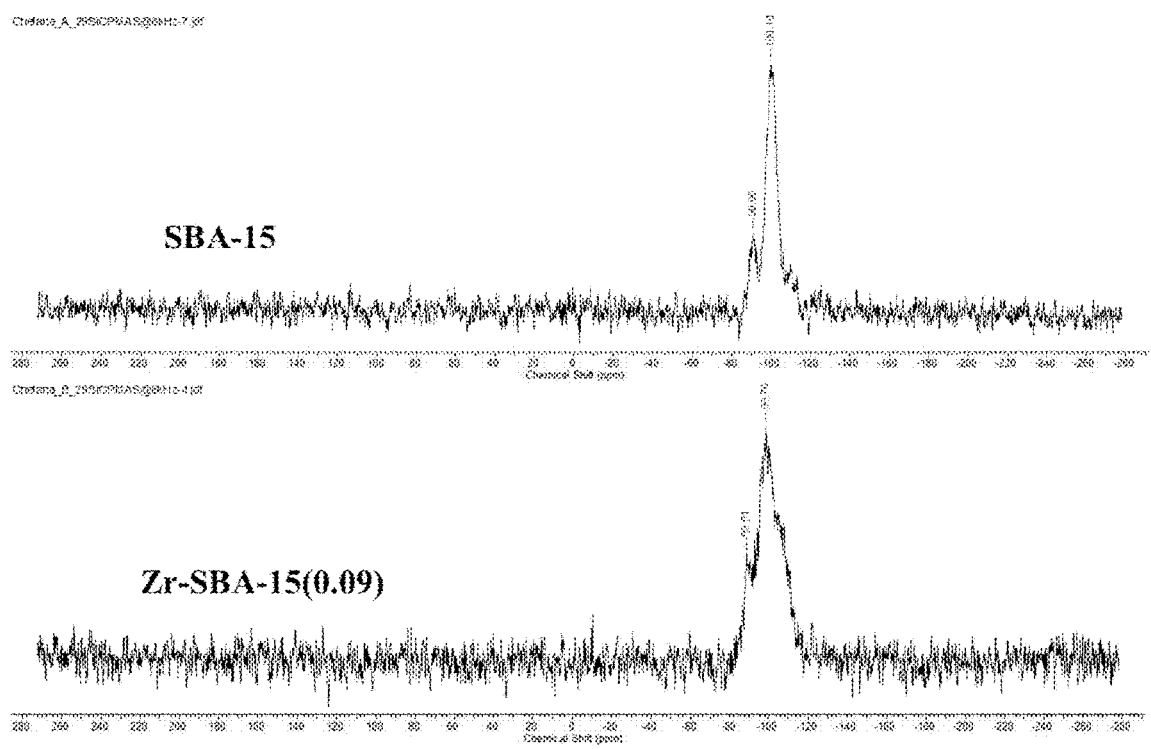
FIG. 9: Solid state $^{29}Si$ NMR for SBA-15 and Zr-SBA-15(0.09)

The FIG. 9 shows that three peaks in the $^{29}Si$ MAS NMR spectra of SBA-15 and Zr-SBA-15(0.09) catalyst at 90 ppm (Q2), 100 ppm (Q3) and 110 ppm (Q4) which are attributed to $(SiO)_2Si(OH)_2$, $(SiO)_3SiOH$ and $(SiO)_4Si$, respectively. The corresponding relative peak areas in $^{29}Si$ MAS NMR spectra. SBA-15 possesses high amount of Q4 species which showed decreasing trend after incorporation of Zr in the framework of SBA-15. The value of (Q3+Q2)/Q4 is higher for Zr-SBA-15(0.09) as compared to SBA-15 i.e. from 18.69 for SBA-15 to 22.60 for Zr-SBA-15(0.09) indicating that the strong interaction existed between SBA-15 framework and Zr.

All these characterization results of XRD, elemental analysis, TEM, $^{29}Si$ NMR revealed that one can incorporate Zr up to 0.09M concentration successfully in the framework of SBA-15. While further increase in concentration of Zr to 0.14 and 0.19 M will not give the SBA-15 structure which is concluded from low angle XRD patterns. Incorporation of Zr in the silica framework generates Lewis acidity which is responsible for catalytic reaction.

Figure 10:
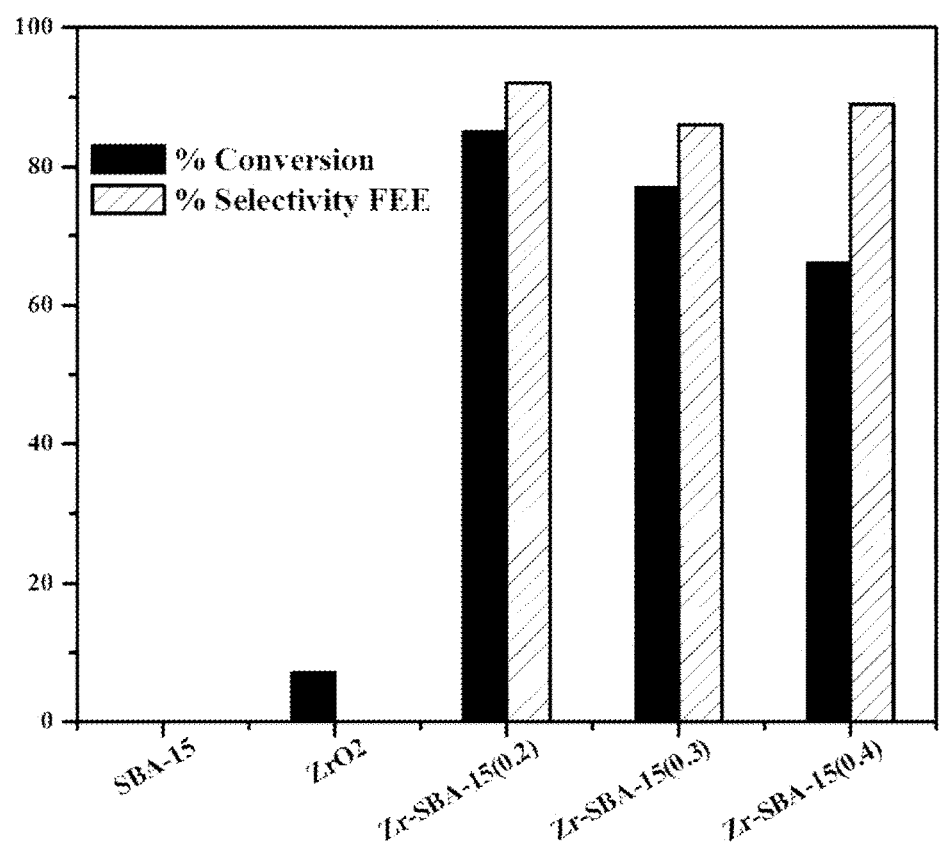
FIG. 10: Catalyst screening for etherification of furfuryl alcohol to Furfuryl ethyl ether. Reaction conditions: Furfuryl alcohol: 3 mmol, Ethanol: 5 ml, Catalyst: 0.1 g, Temp.: 100° C., Time: 5 h

The catalysts are screened for the etherification of furfuryl alcohol using ethanol as solvent in order to evaluate the effect of Zr loading on the conversion of furfuryl alcohol to FEE and data is as presented in FIG. 10. The furfuryl alcohol conversion to FEE did not proceed in absence of the catalyst as well as in presence of parent SBA-15. Pure $ZrO_2$ showed very low conversion for furfuryl alcohol 7% and no FEE product is detected. One pot synthesized Zr-SBA-15 found to be very efficient catalyst for etherification of furfuryl alcohol. For the lowest Zr loading Zr-SBA-15(0.09) it showed the highest conversion for furfuryl alcohol 85% with 92% selectivity towards FEE. As the Zr loading increases for Zr-SBA-15(0.14) and Zr-SBA-15(0.19) it showed decrease in conversion from 77% to 66% along with marginal decrease in selectivity from 86% and 89% respectively. The decrease in conversion of furfuryl alcohol as increase in Zr loading is attributable to less acidity of these catalyst as compare to Zr-SBA-15(0.09). Presence of Lewis acid sites along with uniform mesoporous structure in the Zr-SBA-15 (0.09) catalyst are responsible for the better conversion of furfuryl alcohol and selectivity towards FEE. Further optimization of reaction parameters viz. solvent effect and catalyst loading effect are carried out using Zr-SBA-15 (0.09) as catalyst.

Figure 11:
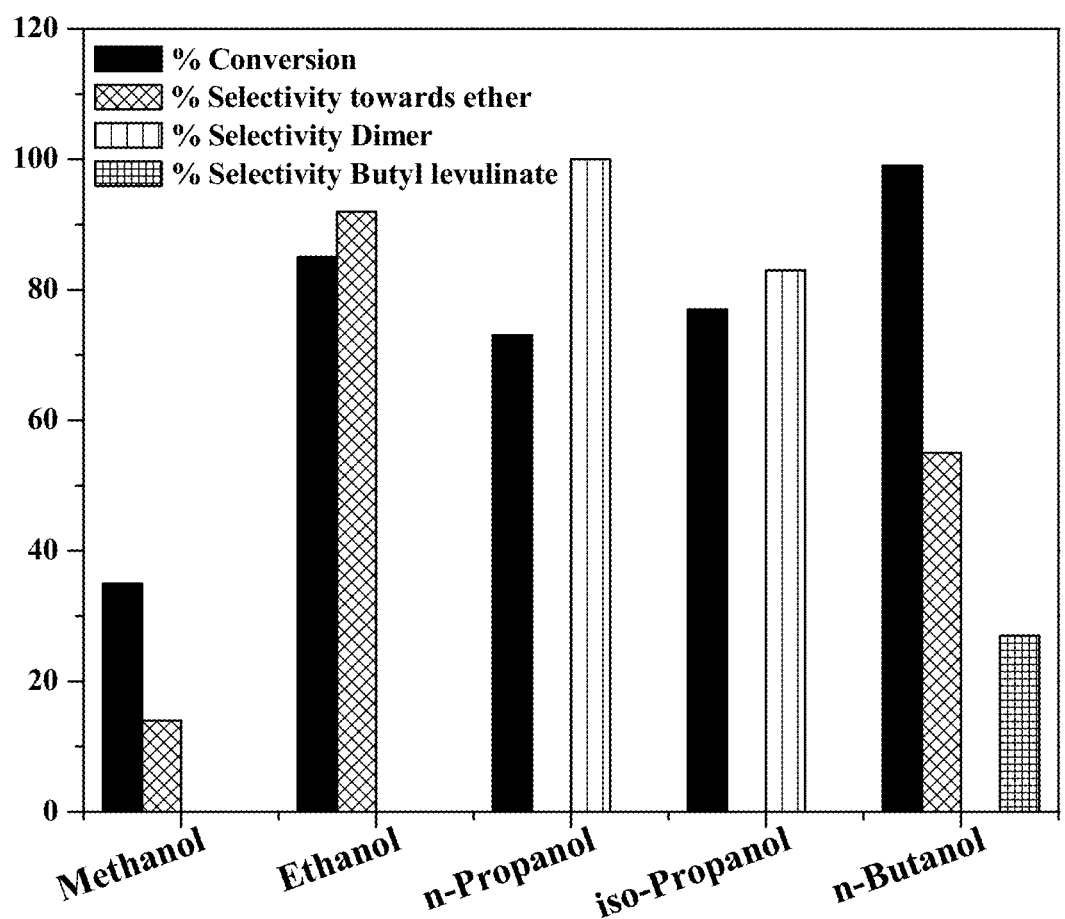
FIG. 11: Effect of solvent on etherification of Furfuryl alcohol using Zr-SBA-15(0.09) as catalyst. Reaction conditions: Furfuryl alcohol: 3 mmol, Ethanol: 5 ml, Catalyst: 0.1 g, Temp.: 100° C., Time: 5 h.

The FIG. 11 shows the effect of various alcohols form C1-C4 on etherification of furfuryl alcohol. It is observed that solvent have very significant role in the etherification of furfuryl alcohol as it alters the conversion and selectivity for the desired product ethers. Methanol as a solvent gives 33% conversion of furfuryl alcohol with 14% selectivity to furfuryl methyl ether. When ethanol is used as solvent the conversion is increased dramatically to 85% with 92% selectivity for desired product. Aggregation of catalyst after adding methanol as the solvent which hinders the interaction between substrate and catalytic active sites must be responsible for lowering the catalytic activity. n-propanol and iso-propanol solvents gives 73% and 77% conversion respectively using Zr-SBA-15(0.09) as catalyst but ether formation is not observed in this case. It is observed that when n-butanol is used as solvent it showed 99% conversion of furfuryl alcohol with 55% selectivity towards ether and 27% selectivity towards butyl levulinate.

Figure 12:
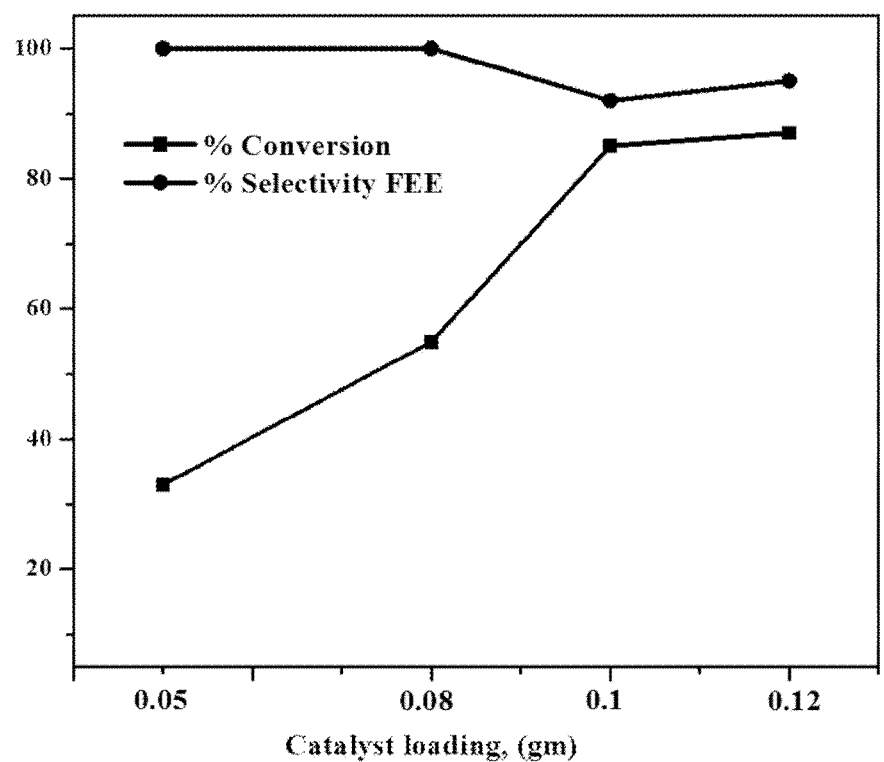
FIG. 12: Effect of catalyst loading. Reaction conditions: Furfuryl alcohol: 3 mmol, Ethanol: 5 ml, Temp.: 100° C., Time: 5 h.

The FIG. 12 shows the effect of catalyst loading in the range of 0.05 to 0.12 g on the etherification of furfuryl alcohol using ethanol as a solvent. 0.05 g loading of Zr-SBA-15(0.09) catalyst gives 33% conversion of furfuryl alcohol with almost complete selectivity towards FEE. It is observed that the increased in catalyst loading results increase in conversion of furfuryl alcohol. For 0.08 g loading it showed 55% conversion and selectively gives FEE as product. Further, it is observed that increase in loading to 0.1 g results in enhanced conversion to 85% with 92% selectivity towards FEE. Further increase in catalyst loading to 0.12 g showed marginal increase in conversion i.e. 87% with 95% selectivity for desired product.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Catalyst Preparation

SBA-15 was prepared according to previously published [*Science*. 1998, 279, 548-552]. Compositions for Zr incorporated synthesis solution was 0.013 P123:1 TEOS: 1NaCl: 0.09-0.19 ZrOCl$_2$.8H$_2$O:221 H$_2$O. In a typical procedure 1.5 g of pluronic P123 and 1.8 g of NaCl was dissolved in 70 g de-ionized water, stirred for 3 h at 35° C. in teflon beaker. 4.2 g of TEOS was added. After hydrolysis for 4 h, a pale white colloidal solution with a pH value of 4-5 was obtained. To this solution 10 ml of ZrOCl$_2$.8H$_2$O solution concentration ranging from 0.09 to 0.19 M was added. The pH value of the synthesis solution dropped to 2 and solutions became transparent. The solution was stirred for 24 h at 35° C. The milky suspension was aged at 90° C. for 24 h in teflon lined steel autoclave. The solid product was filtered, washed, dried at 100° C. for 12 h and calcined at 500° C. for 6 h (heating rate @ 1° C. min$^{-1}$). The resulting samples were labeled as Zr-SBA-15(0.09), Zr-SBA-15(0.14), and Zr-SBA-15(0.19) where bracketed figures indicate molarity of ZrOCl$_2$.8H$_2$O added during preparation.

a) Catalyst Characterization

Low angle powder X-ray diffractograms were collected on a Rigaku D MAX III VC diffraction system using Ni-filtered Cu Kα radiation (X, =1.5404 Å) over a 2θ range of 0.5-5° with a scan speed of 2° per minute. Wide-angle X-ray diffraction (WA-XRD) were recorded on a PANalytical PXRD model X-Pert PRO-1712, using Ni filtered Cu Kα radiation (λ=0.154 nm) as a source (current intensity, 30 mA; voltage, 40 kV) and a X-celerator detector. The specific surface area, total pore volume, and average pore diameter were measured by N$_2$ adsorption-desorption method using a Quantachrome Autosorb-1C sorption unit. Diffuse reflectance UV-Vis measurements were carried out on a Shimadzu spectrophotometer (model UV-2550) with spectral-grade BaSO4 as reference material. NH$_3$-TPD experiments were carried out on a Micromeritics-2720 (ChemisoftTPx) instrument. Transmission electron microscopy (TEM) analysis was performed on a Jeol Model JEM 1200 electron microscope operated at an accelerating voltage of 120 kV. Morphology of SBA-15 and Zr incorporated SBA-15 catalysts were examined by scanning electron microscopy (SEM), and the presence of Zr was confirmed by EDX analysis on a LEO-LEICA STEREO SCAN 440 instrument. FT-IR was performed on a PerkinElmer Frontier instrument in ATR (PIKE Tech) mode at room temperature. Pyridine IR was conducted using a Harrick diffuse reflectance praying mantis assembly. The reaction was monitored by analyzing the liquid products using a Shimadzu QP-2010 Ultra GC-MS. Solid-state MAS CP-NMR of the catalyst samples were carried out using a JEOL-400 MHz instrument.

Example 2: Etherification of Furfuryl Alcohol to FEE

Etherification of furfuryl alcohol was carried out in a two necked 100 ml round bottom flask equipped with reflux condenser. In one pot reaction, 3 mmol of furfuryl alcohol (296 mg), ethanol (5 ml) and catalyst (100 mg) was added and the reaction was continued at 100° C. for 5 h after which, the catalyst was recovered by filtration. The reaction mixtures were quantified by GC (Shimadzu 2025) using FFAP column equipped with flame ionization detector. Identification of products was done by GC-MS. The conversion of furfuryl alcohol and selectivity of FEE were calculated by the following equations, $$(\%) \text{ Conversion of furfuryl alcohol} = \frac{(\text{Initial moles of furfuryl alcohol} - \text{moles of furfuryl alcohol unreacted})}{\text{Initial moles of furfuryl alcohol}} * 100 \quad (I)$$

$$(\%) \text{ Selectivity of product} = \frac{\text{moles of desired product formed}}{\Sigma \text{Total moles of product formed}} * 100 \quad (II)$$

a) Recycling of Catalyst

At the end of reaction, the catalyst was recovered by filtration. The recovered catalyst was washed three times with 10 ml ethanol and dried at 120° C. overnight in a vacuum oven. Catalyst was calcined at 400° C. for 4 h. The recycled catalyst was used for the same reaction study.

Example 3: Etherification of Furfuryl Alcohol with Different Alcohols

Etherification of furfuryl alcohol was carried out in a two necked 100 ml round bottom flask equipped with reflux condenser. In one pot reaction, 3 mmol of furfuryl alcohol (296 mg), methanol or n-propanol or iso-propanol or n-butanol (5 ml) and catalyst (100 mg) was added and the reaction was continued at 100° C. for 5 h after which, the catalyst was recovered by filtration. The reaction mixtures were quantified by GC (Shimadzu 2025) using FFAP column equipped with flame ionization detector.

Advantages of Invention

1. An environmentally friendly provided.
2. Single step process
3. Biomass utilization
4. Efficient catalyst system
5. Excellent selectivity to FEE which can be used as gasoline component.
6. High conversion of furfuryl alcohol achieved.

The invention claimed is:

1. A single step process for the synthesis of furfuryl ethyl ether comprises refluxing the reaction mixture of furfuryl alcohol, ethanol and Zr incorporated SBA-15 catalyst at temperature in the range of 80 to 120° C. for the period in the range of 3 to 7 hrs to afford furfuryl ethyl ether, wherein selectivity of said reaction towards furfuryl ethyl ether is in the range of 85 to 95%.

2. The process as claimed in claim 1, wherein said reaction is carried out at temperature in the range of 90 to 100° C.

3. The process as claimed in claim 1, wherein said reaction is carried out for the period in the range of 5 to 6 hrs.

4. The process as claimed in claim 1, wherein conversion of furfuryl alcohol is in the range of 60 to 90%.

* * * * *